United States Patent
Morita (10) Patent No.: US 12,324,640 B2
(45) Date of Patent: Jun. 10, 2025

(54) MEDICAL ROBOT

(71) Applicant: RIVERFIELD INC., Tokyo (JP)

(72) Inventor: Naoya Morita, Tokyo (JP)

(73) Assignee: RIVERFIELD INC., Tokyo (JP)

(*) Notice: Subject to any disclaimer, the term of this patent is extended or adjusted under 35 U.S.C. 154(b) by 349 days.

(21) Appl. No.: 17/876,133

(22) Filed: Jul. 28, 2022

(65) Prior Publication Data

US 2023/0000575 A1    Jan. 5, 2023

Related U.S. Application Data

(63) Continuation of application No. PCT/JP2020/006364, filed on Feb. 18, 2020.

(51) Int. Cl.
*A61B 34/30* (2016.01)
*A61B 34/00* (2016.01)

(52) U.S. Cl.
CPC ............. *A61B 34/30* (2016.02); *A61B 34/74* (2016.02); *A61B 2034/305* (2016.02)

(58) Field of Classification Search
None
See application file for complete search history.

(56) References Cited

U.S. PATENT DOCUMENTS

| | | | |
|---|---|---|---|
| 2010/0234857 A1 | 9/2010 | Itkowitz et al. | |
| 2017/0252002 A1* | 9/2017 | Mine | A61B 8/4218 |
| 2018/0235724 A1 | 8/2018 | Nowatschin et al. | |
| 2018/0243921 A1* | 8/2018 | Hashimoto | B25J 19/028 |

FOREIGN PATENT DOCUMENTS

| | | |
|---|---|---|
| CN | 201631383 U | 11/2010 |
| CN | 108135660 A | 6/2018 |
| EP | 3 130 305 A1 | 2/2017 |
| JP | 2005-118457 A | 5/2005 |
| JP | 2005-192743 A | 7/2005 |
| JP | 2016-93493 A | 5/2016 |
| JP | 2018-111142 A | 7/2018 |
| JP | 2019-517859 A | 6/2019 |
| WO | 2016/071674 A1 | 5/2016 |
| WO | 2017/048736 A1 | 3/2017 |

(Continued)

OTHER PUBLICATIONS

Chinese Office Action dated Jan. 4, 2023 in Chinese Application No. 202080086009.2.

(Continued)

*Primary Examiner* — Jared Fureman
*Assistant Examiner* — Aqeel H Bukhari
(74) *Attorney, Agent, or Firm* — Sughrue Mion, PLLC (57) ABSTRACT

A medical robot includes an arm, a controller that controls driving of the arm, a holding body that is connected to the arm at a connection portion and holds a held body, and a selector switch provided on the holding body for selectively switching between a control state in which the driving of the arm is controlled by the controller and a manual state in which control by the controller is released. The controller performs control of switching between the control state and the manual state based on an operation signal from the selector switch.

19 Claims, 10 Drawing Sheets

(56) References Cited

FOREIGN PATENT DOCUMENTS

WO    2017/205308 A1    11/2017

OTHER PUBLICATIONS

Japanese Office Action dated May 11, 2021 in Japanese Application No. 2021-517489.
International Search Report of PCT/JP2020/006364 dated Apr. 21, 2020 [PCT/ISA/210].
Office Action dated Nov. 15, 2022 issued by the European Patent Office in European Patent Application 20919654.2.
Supplementary European Search Report dated Nov. 3, 2022 in European Application No. 20919654.2.

* cited by examiner

FIG. 10

MEDICAL ROBOT

CROSS-REFERENCE TO RELATED APPLICATION

This U.S. application is a continuation of International Application No. PCT/JP2020/006364, filed Feb. 18, 2020, the entire contents of which is incorporated by reference herein in its entirety.

BACKGROUND

The present disclosure relates to a medical robot including an arm unit capable of holding an endoscope, a treatment tool, or camera, etc.
A medical robot includes an arm unit configured to be controlled such that a treatment tool can be placed at a desired position. A drive control of the arm unit may be released in order to, for example, make adjustments upon introduction of a held body that is held by the arm unit into a patient's body or making settings during treatment, etc. However, the location of a mechanism for releasing the drive control may result in various difficulties in releasing the drive control to allow adjustments and/or setting to be made.

SUMMARY

It is an aspect to provide a medical robot including a selector switch that selectively switches between a control state in which the driving of an arm unit is controlled and a manual state in which control by a control unit is released.

According to an aspect of one or more embodiments, there is provided a medical robot comprising an arm unit; a controller that controls driving of the arm unit; a holding body that is provided at the arm unit at a connection portion and holds a held body; and a selector switch provided on the holding body for selectively switching between a control state in which the driving of the arm unit is controlled by the controller and a manual state in which control by the controller is released, wherein the controller performs control of switching between the control state and the manual state based on an operation signal from the selector switch.

According to another aspect of one or more embodiments, there is provided a medical robot comprising an arm; a controller configured to drive the arm; and a holding body provided at a tip of the arm, the holding body comprising: a holder provided at a front end in an extending direction of the holding body, and a selector switch provided at a rear end in the extending direction of the holding body, wherein the selector switch is configured to switch between a control state in which the driving of the arm unit is controlled by the controller and a manual state in which control by the controller is released.

BRIEF DESCRIPTION OF DRAWINGS

The above and/or other aspects will become apparent and more readily appreciated from the following description of various embodiments, taken in conjunction with the accompanying drawings of which:

FIGS. 5A and 5B are enlarged views illustrating the selector switch in the holding body illustrated in FIG. 2, according to some embodiments, wherein

DETAILED DESCRIPTION

As a robot for holding an endoscope, for example, a surgical assistance system has been proposed. The surgical assistance system is composed of a base unit and a robot mechanism. The robot mechanism has a support column, a first robot arm that is attached to the tip of the support column so as to be rotatable, a second robot arm that is attached to the tip of the first robot arm so as to be rotatable, and a device support that is attached to the tip of the second robot arm. The device support is configured to accommodate an endoscope or other medical tool or device.

In a medical robot, an arm unit holds a body to be held, such as an endoscope, a treatment tool, or a camera, and is driven and controlled thereby to place the held body at a desired position, and the held body performs an operation that is set. It is, however, often necessary to release the drive control of the arm unit to manually operate the arm unit, such as when making adjustments upon introduction of the held body into the patient's body or making detailed settings during treatment.

In order to release such drive control, however, the practitioner has to move away from the arm unit and temporarily suspend the operation of the medical robot because the practitioner needs to operate the medical robot main body, that is, operate the release switch of the medical robot main body. In this regard, if the above release switch is provided on the arm unit, the practitioner can perform the release operation without moving away from the arm unit.

On the other hand, a master-slave type system is being adopted, which is composed of a master machine operated by the practitioner and a robot as a slave machine that operates under the control by the master machine. In such a system, in addition to the practitioner who operates the master machine, an assistant who assists the operation of the slave machine placed away from the master machine is in charge. In such a system, the assistant needs to work while moving around the medical robot or the surgical table, and even if the release switch is provided on the arm unit, the assistant has to move, for example, around the surgical table for the operation of the release switch. In addition, it is often difficult to change the placement of each part of the medical robot during the treatment due to the relationship between each part of the robot and the diseased site of the patient on the surgical table. In such a case, there is a problem in that the operation of the release switch will be difficult because the posture of the assistant who operates the switch is limited.

Moreover, in recent medical robots and surgical systems including medical robots, there may be employed a configuration in which the arm unit, the main body, etc. are arranged so as to be close to each other in a smaller size than before or a configuration in which a plurality of arm units is arranged so as to be close to each other. In such a configuration, the practitioner or assistant cannot take a free posture because there are adjacent members or the like in the way, and the operation of the release switch may be difficult. Furthermore, a peripheral device may incidentally contact the above release switch to release the drive control of the arm unit or cause the arm unit to return from the release state to the drive control state.

It is an aspect to provide a medical robot including a selector switch that selectively switches between a control state in which the driving of an arm unit is controlled and a manual state in which control by a control unit is released, wherein the medical robot allows a practitioner or an assistant to operate the selector switch in a short time regardless of the posture of the medical robot or the ambient environment and can prevent the selector switch from operating due to contact with an adjacent member or an erroneous operation by the practitioner or the like.

According to some embodiments, there is provided a medical robot that includes an arm unit, a control unit, a holding body, and a selector switch. The control unit controls driving of the arm unit. The holding body is connected to the arm unit at a connection portion and holds a held body. The selector switch is provided on the holding body for selectively switching between a control state in which the driving of the arm unit is controlled by the control unit and a manual state in which control by the control unit is released. The selector switch is disposed on at least one of both sides of a reference plane including an extending direction of the arm unit and an extending direction of the held body. The control unit performs control of switching between the control state and the manual state based on an operation signal from the selector switch.

According to various embodiments, the selector switch may be provided on the holding body so as to be located on the opposite side to the held body with respect to the connection portion in the extending direction of the held body.

According to various embodiments, the selector switch may be provided with a prevention section that prevents the switching between the control state and the manual state due to contact with an interfering body located around the selector switch.

According to various embodiments, the prevention section may be achieved by the selector switch, and the selector switch may be configured to: output a control signal for the control unit to switch from the control state to the manual state when the selector switch is pressed inside the holding body; and output a control signal for the control unit to return from the manual state to the control state when pressing of the selector switch is released.

According to various embodiments, the prevention section may be achieved by the selector switch, and the selector switch may be configured to output a control signal for the control unit to switch between the control state and the manual state each time the selector switch is pressed inside the holding body.

According to various embodiments, the selector switch may be a switch that operates when pressed for a predetermined time or longer.

According to various embodiments, the selector switch may have a first selector switch provided on one side of the reference plane and a second selector switch provided on the other side, and the control unit may switch between the control state and the manual state based on the operation signal from one of the first selector switch and the second selector switch.

According to various embodiments, the control unit may be configured to: provided that the control of switching from the control state to the manual state is carried out based on the operation signal output from the first selector switch, carry out the control of returning from the manual state to the control state when another version of the operation signal output from the first selector switch is input; and provided that the control of switching from the control state to the manual state is carried out based on the operation signal output from the second selector switch, carry out the control of returning from the manual state to the control state when another version of the operation signal output from the second selector switch is input.

According to various embodiments, the holding body may include a rotation mechanism that enables the held body to rotate relative to the holding body about the extending direction of the held body.

According to various embodiments, the selector switch may be provided so that the relative position with respect to the holding body is kept when the held body is rotating relative to the holding body.

According to various embodiments, the medical robot may include at least one second arm unit in addition to a first arm unit as the arm unit provided with the holding body on which the selector switch is provided, and the interfering body preferably includes the second arm unit located around the first arm unit.

According to various embodiments, the second arm unit may be provided with a holding body and a selector switch equivalent to the holding body and the selector switch for the first arm unit, respectively.

According to various embodiments, a medical robot may allow a practitioner himself/herself or an assistant to operate the selector switch in a short time and that can prevent the selector switch from operating due to contact with an adjacent member or an erroneous operation by the practitioner or the like. In a master-slave type system or a surgical robot having a complicated configuration, the medical robot can be provided in which the selector switch can be easily operated without imposing a heavy burden on the practitioner or assistant even when the approach to the selector switch is limited due to the posture of the robot's arm unit or the relationship with a peripheral device.

Figure 1:
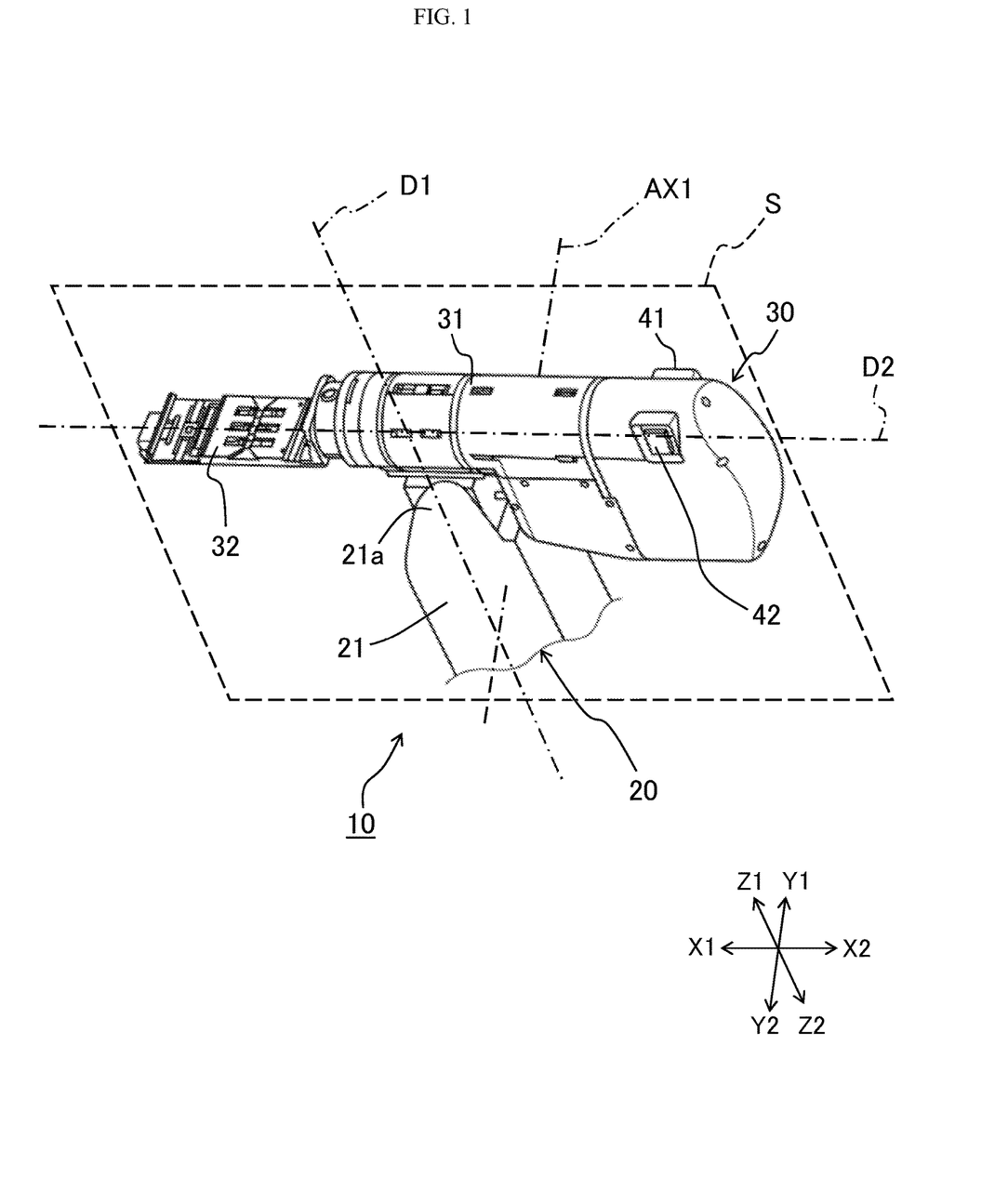
FIG. 1 is a perspective view illustrating a part of the medical robot according to some embodiments.
Figure 2:
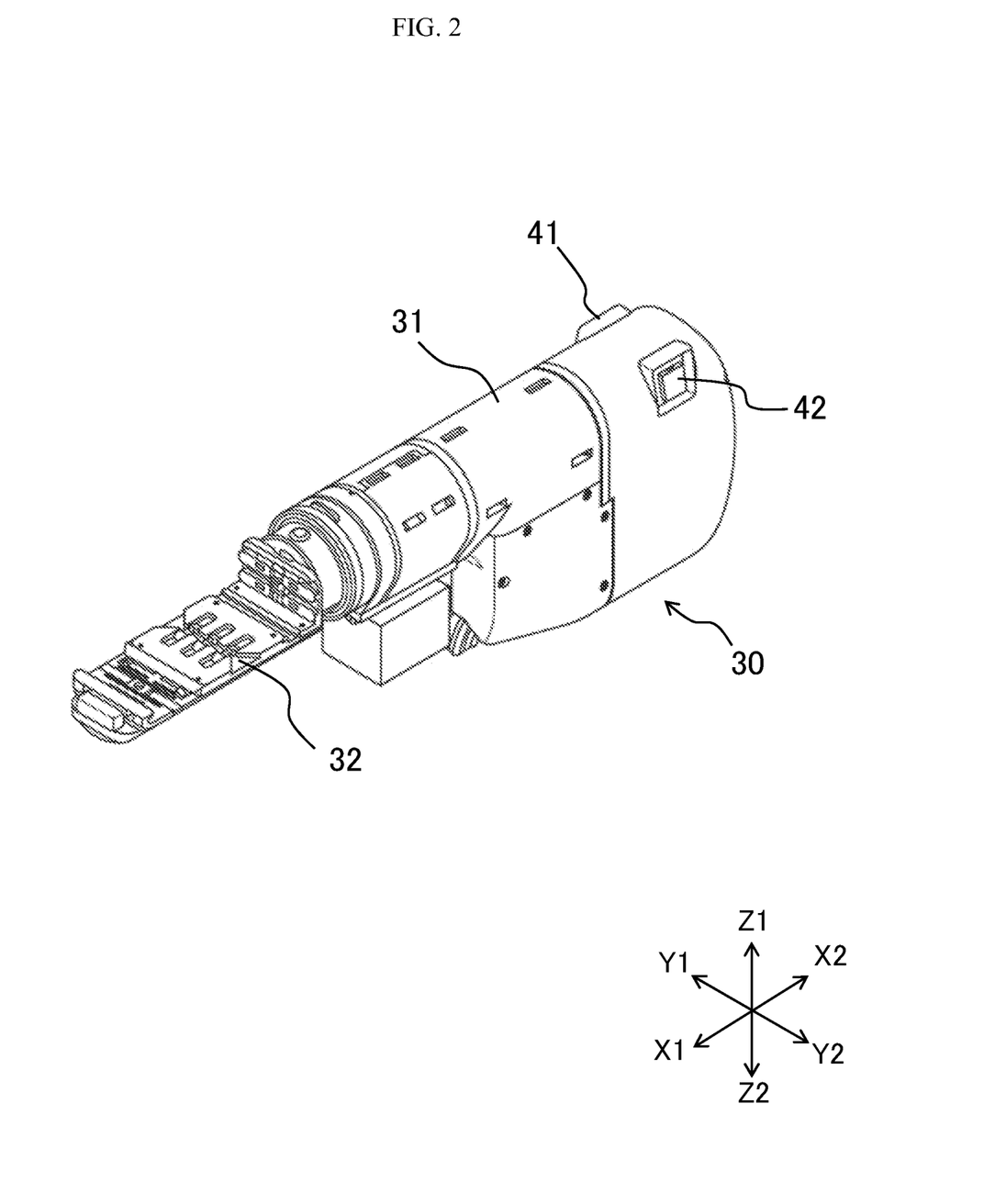
FIG. 2 is a perspective view illustrating the configuration of a holding body according to some embodiments.
Figure 3:
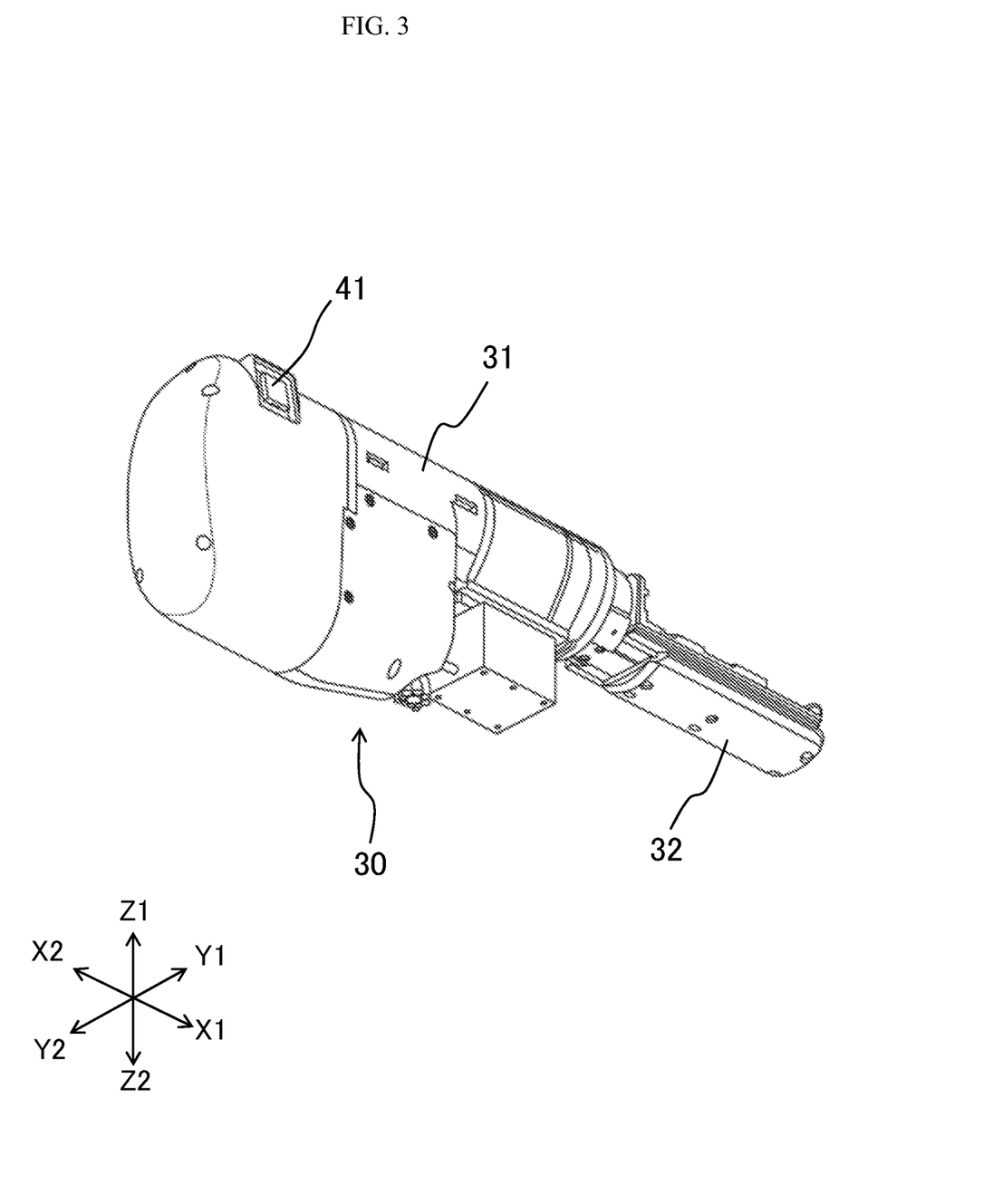
FIG. 3 is a perspective view illustrating the configuration of the holding body according to some embodiments.
Figure 4A:
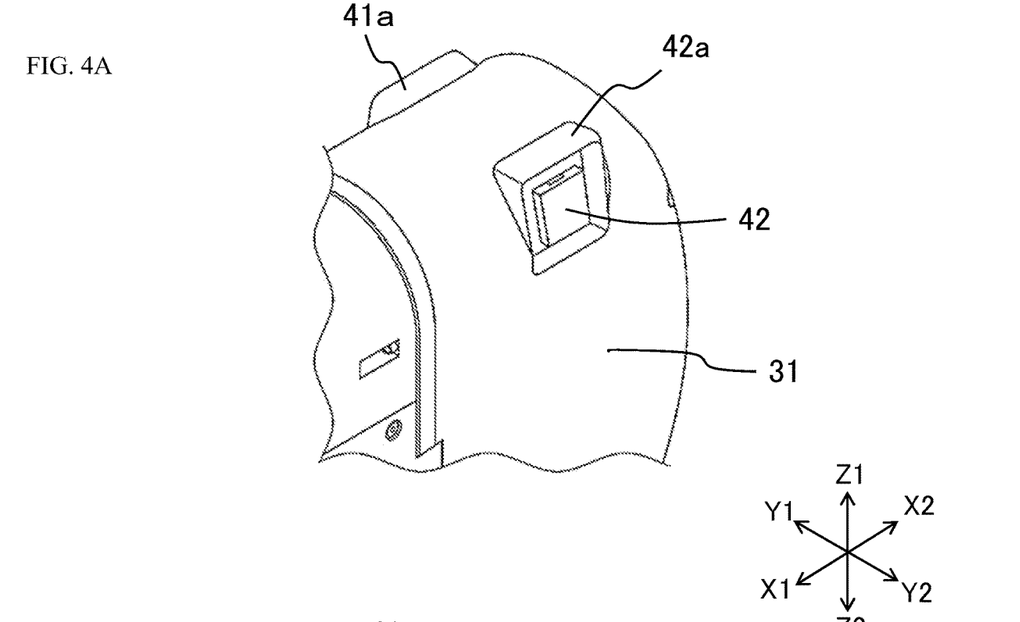
FIGS. 4A and 4B are enlarged perspective views illustrating selector switches of the holding body illustrated in FIGS. 2 and 3, respectively, according to some embodiments.
Figure 4B:
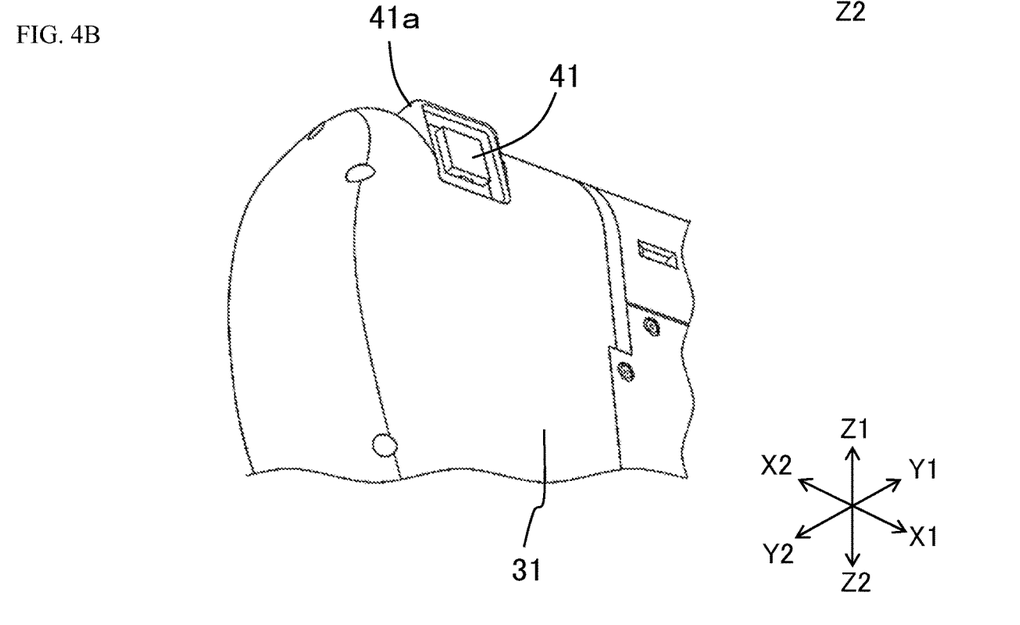
Figure 5A:
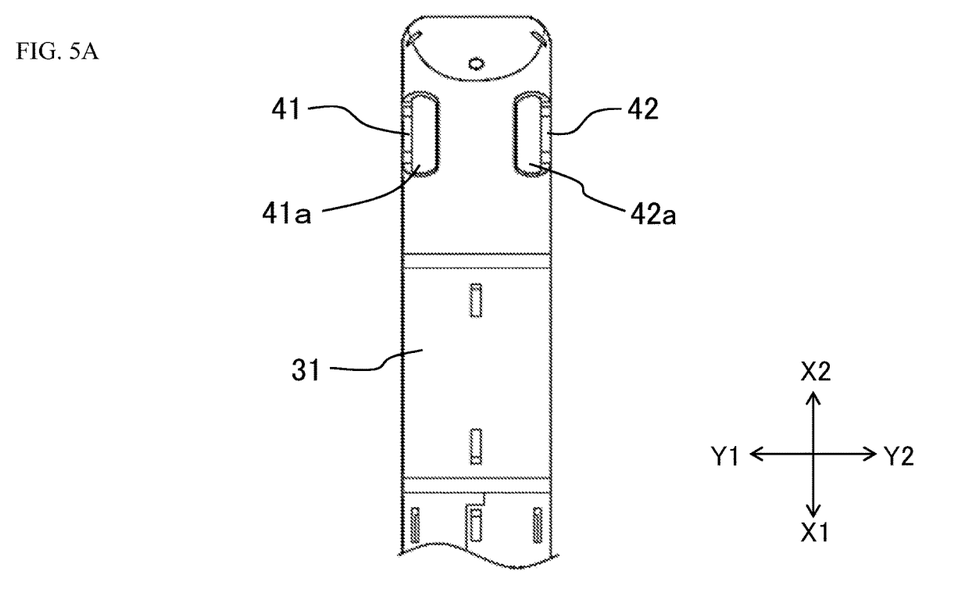
FIG. 5A is a plan view and FIG. 5B is a rear view.
Figure 5B:
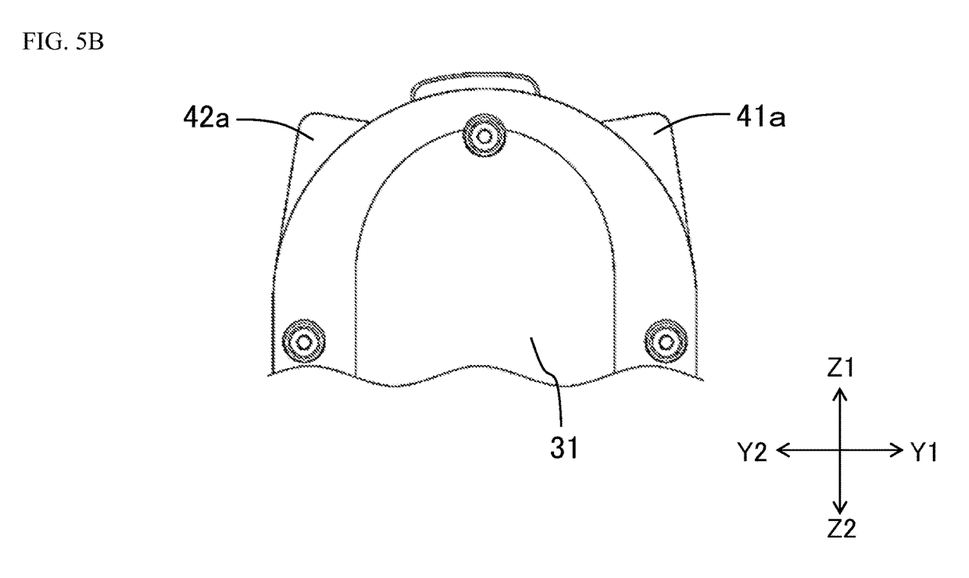

Hereinafter, the medical robot according to one or more embodiments will be described in detail with reference to the drawings. FIG. 1 illustrates a configuration as a part of a medical robot 10 in which a holding body 30 is provided on an arm 21 of an arm unit 20. FIG. 2 is a perspective view of the holding body 30 as viewed from the front upper side, and FIG. 3 is a perspective view of the holding body 30 as viewed from the rear lower side. FIG. 4A is an enlarged view of the rear part of the holding body 30 illustrated in FIG. 2, and FIG. 4B is an enlarged view of the rear part of the holding body 30 illustrated in FIG. 3. In each figure, X-Y-Z coordinates are illustrated as reference coordinates. In the following description, the Z1-Z2 direction is referred to as an up-down direction, the X1-X2 direction is referred to as a front-rear direction, and the Y1-Y2 direction is referred to as a right-left direction. The X1-X2 direction and the Y1-Y2 direction are perpendicular to each other, and the X-Y plane including the X1-X2 direction and the Y1-Y2 direction is perpendicular to the Z1-Z2 direction.

As illustrated in FIG. 1, the medical robot 10 of some embodiments includes an arm unit 20 and a holding body 30 provided on the arm unit 20, and the holding body 30 is provided with a pair of selector switches 41 and 42. The medical robot 10 may have another configuration in which, in addition to the above arm unit 20 (first arm unit), one or more arm units (second arm unit or units) are provided, each including a holding body and selector switches similar to the above holding body 30 and the above selector switches 41 and 42.

The arm unit 20 includes an arm 21. The arm 21 extends along a first direction D1 inclined upward with respect to the front-rear direction (X1-X2 direction) and is connected to a main body portion 31 of the holding body 30 at a connection portion 21a provided at the tip of the arm 21. The connection portion 21a supports the holding body 30 in a rotatable manner around a first axis of rotation AX1.

Here, the configuration of the arm unit 20 is not limited to the configuration illustrated in FIG. 1. In another configuration, for example, the arm 21 may be connected to a second arm via a joint unit and configured to rotate or bend within a predetermined angle range with respect to the second arm by an action of the joint unit, or a third arm may be provided with respect to the second arm via a further joint unit.

In some embodiments, the arm unit 20 is driven by a drive unit 52 that is driven based on a control signal from a controller 51 (FIG. 6), and by driving the arm 21, the position and posture of the holding body 30 can be set arbitrarily. Each arm of the arm unit 20 is driven by mechanical drive, pneumatic drive, or the like. The controller may be, for example, one or more microprocessors or one or more central processing units (CPUs) adapted to control various components of the medical robot according to control signals generated and transmitted from the controller.

The holding body 30 includes the main body portion 31 and a holder 32 that extends forward from the front end of the main body portion 31. The holder 32 is configured to be rotatable relative to the main body portion 31 about a central axis along the front-rear direction (X1-X2 direction). The holder 32 is rotated by driving a built-in motor 53 that is embedded in the main body portion 31, and the motor 53 is driven in response to a control signal from the controller 51 (see FIG. 6).

The holder 32 may be equipped with a treatment tool as a held body to be inserted into the patient's body so that the treatment tool extends along the front-rear direction (X1-X2 direction, second direction D2).

Examples of the held body include an endoscope in addition to the treatment tool. Examples of the held body may further include a camera capable of capturing images of the appearance of the patient's diseased site or the like without inserting the camera into the patient's body.

The first selector switch 41 and the second selector switch 42 are provided at the right and left positions, respectively, on the rear upper part of the main body portion 31 of the holding body 30. In the main body portion 31, these two selector switches 41 and 42 may be provided at positions corresponding to each other in the up-down direction (Z1-Z2 direction) and the front-rear direction (X1-X2 direction) and are arranged so as to form a pair.

Figure 7A:
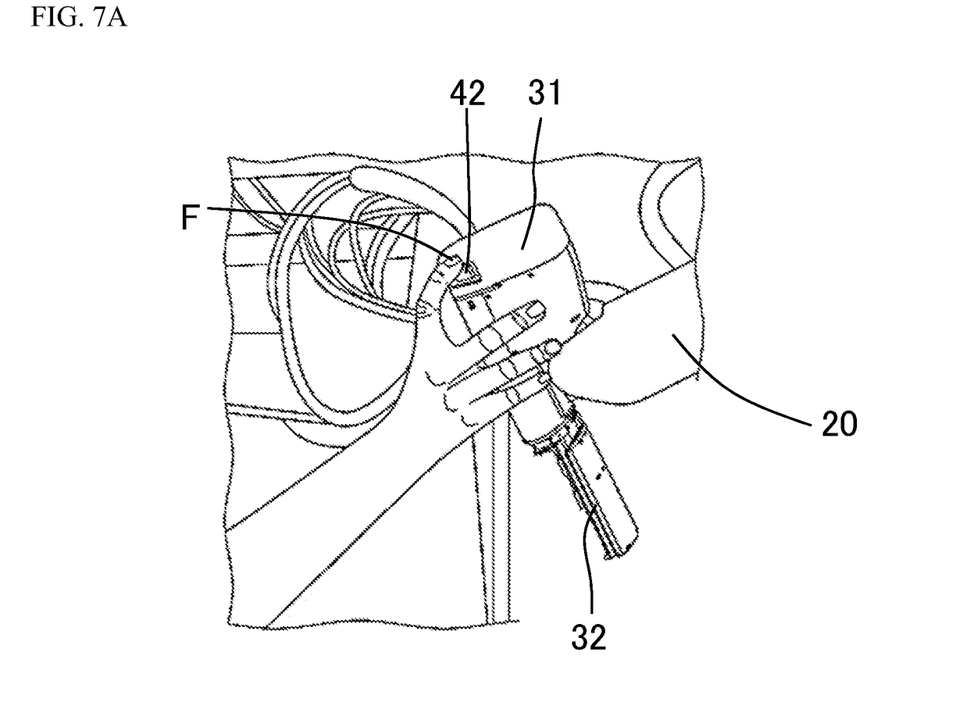
FIGS. 7A and 7B are explanatory views each illustrating a state in which a practitioner is operating from the side a selector switch of a holding body, according to some embodiments.
Figure 7B:
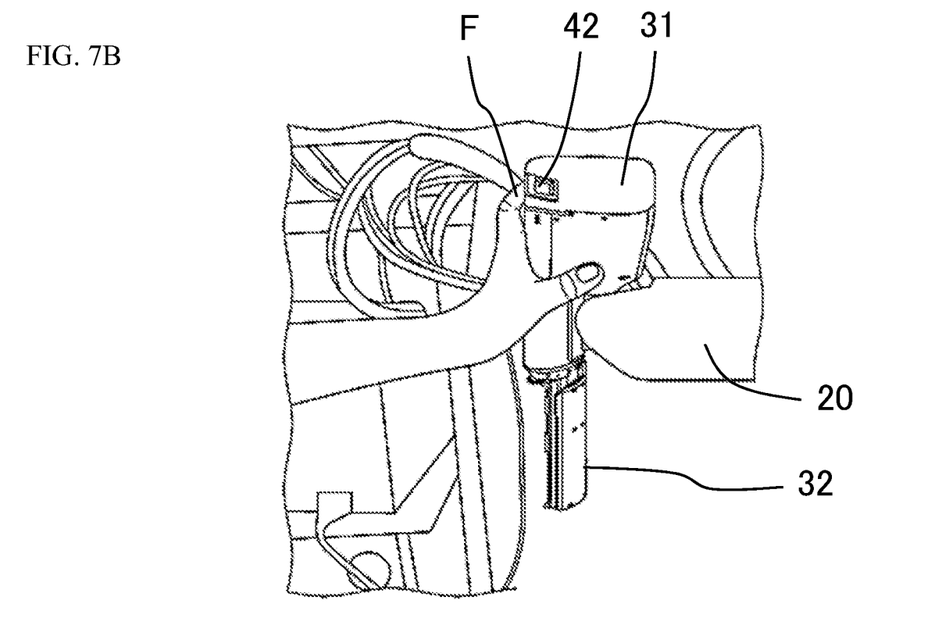

As illustrated in FIGS. 7A and 7B, for example, when operating the main body portion 31 which faces approximately downward, the practitioner can press the first selector switch 41 or the second selector switch 42 with a fingertip F to operate it while touching/holding the main body portion 31 with the palm and/or fingers. FIG. 7A illustrates a state in which the practitioner performs the operation with the right index finger F while holding the main body portion 31 from the side with the right palm and the like, and FIG. 7B illustrates a state in which the practitioner performs the operation with the left index finger F while holding the main body portion 31 from the side with the left palm and the like. Thus, the practitioner can perform the operation with any of the right and left hands depending on the availability of his/her both hands and the distance from a peripheral device.

Figure 8A:
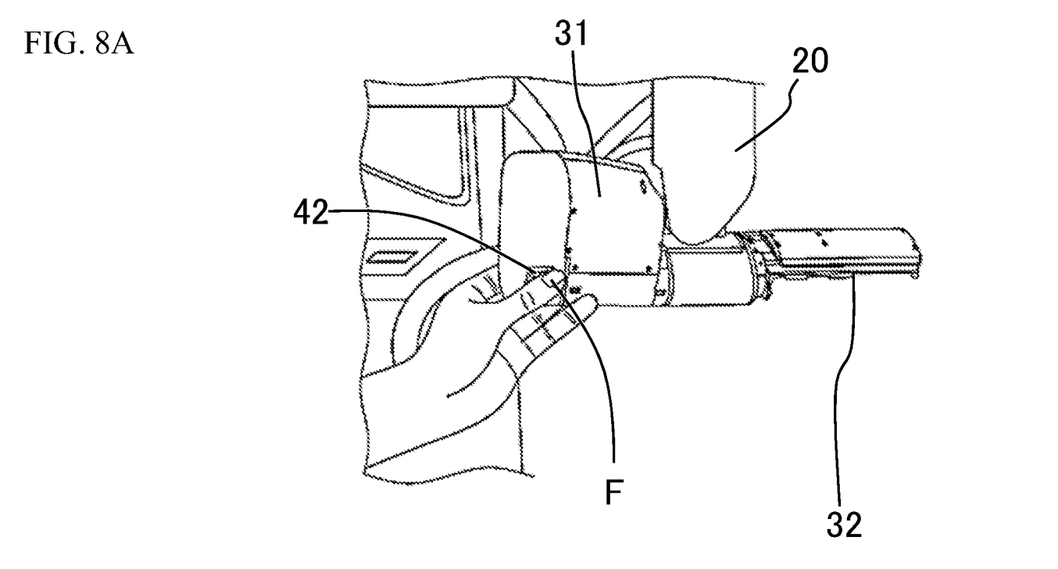
FIGS. 8A and 8B are explanatory views each illustrating a state in which a practitioner is operating from below a selector switch of a holding body, according to some embodiments.
Figure 8B:
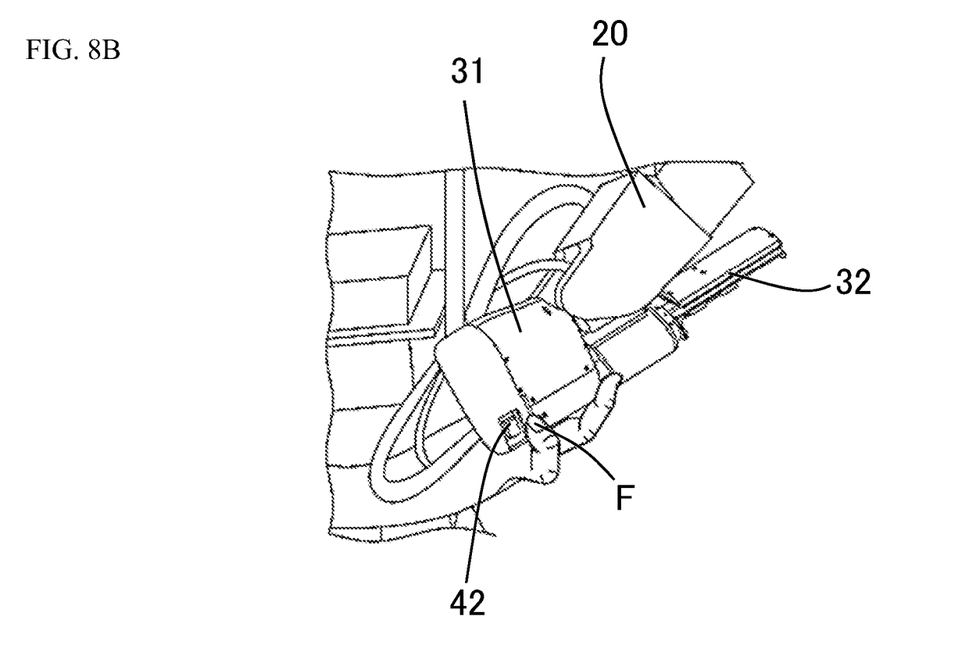

In the examples illustrated in FIGS. 8A and 8B, the practitioner operates the main body portion 31 in an approximately horizontal state. FIG. 8A illustrates a state in which the practitioner performs the operation with the left thumb F while holding the main body portion 31 from below the side with the left fingers, and FIG. 8B illustrates a state in which the practitioner performs the operation with the right index figure F while holding the main body portion 31 from below with the right palm and the like. Thus, the practitioner can perform the operation while holding the main body portion 31 from below depending on the orientation of the main body portion 31.

Figure 9:
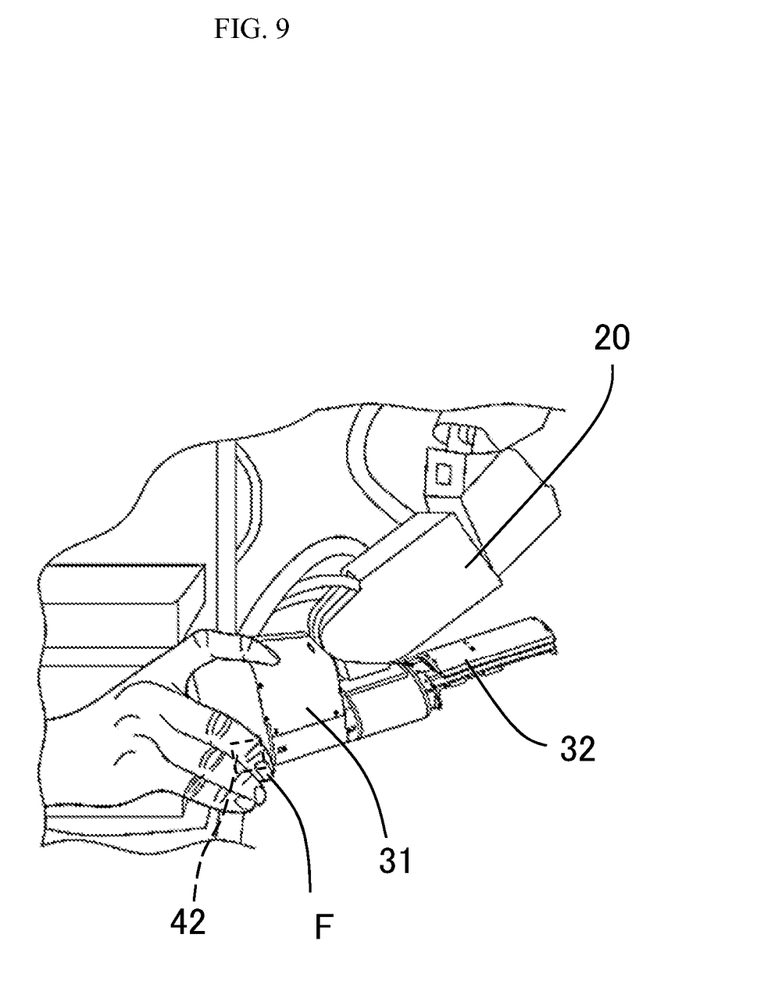
FIG. 9 is a diagram illustrating an example configuration of a state in which a practitioner is operating from above the side a selector switch of the holding body which faces approximately sideways, that is, a state in which the second selector switch is pressed with the right middle finger or ring finger, according to some embodiments.

In the example illustrated in FIG. 9, the practitioner holds from above the side the main body portion 31 which is in an approximately horizontal state. By providing the two selector switches 41 and 42 in a predetermined range on the rear upper part of the main body portion 31, the main body portion 31 in an approximately horizontal state as in FIGS. 8A and 8B can be held from different directions. Thus, the degree of freedom in the posture during the operation is increased, and the most well-balanced holding position can be arbitrarily selected in relation to the support position by the connection portion 21a of the arm unit 20.

The two selector switches 41 and 42 are arranged so that a reference plane S (see FIG. 1) is interposed therebetween. More specifically, when the reference plane S is defined as a plane that includes a first direction D1 in which the arm 21 of the arm unit 20 extends and a second direction D2 (front-rear direction) in which the held body attached to the holder 32 extends, that is, a plane that is orthogonal to the right-left direction (Y1-Y2 direction) and passes the holding body 30 at the center in the right-left direction, the first selector switch 41 is disposed on one side of the reference plane S while the second selector switch 42 is disposed on the other side of the reference plane S. Thus, the two selector switches 41 and 42 are arranged at respective positions symmetrical with respect to the reference plane S.

In addition, the two selector switches 41 and 42 are provided so as to be located on the opposite side to the holder 32 and the held body with respect to the connection portion 21a in the extending direction of the held body (X1-X2 direction). Through this configuration, when in the manual state, it is easy to balance with the weight of the held body located on the front side, and the rotating operation can be easily performed, which is centered on the first axis of rotation AX1 with the connection portion 21a as a fulcrum.

Figure 6:
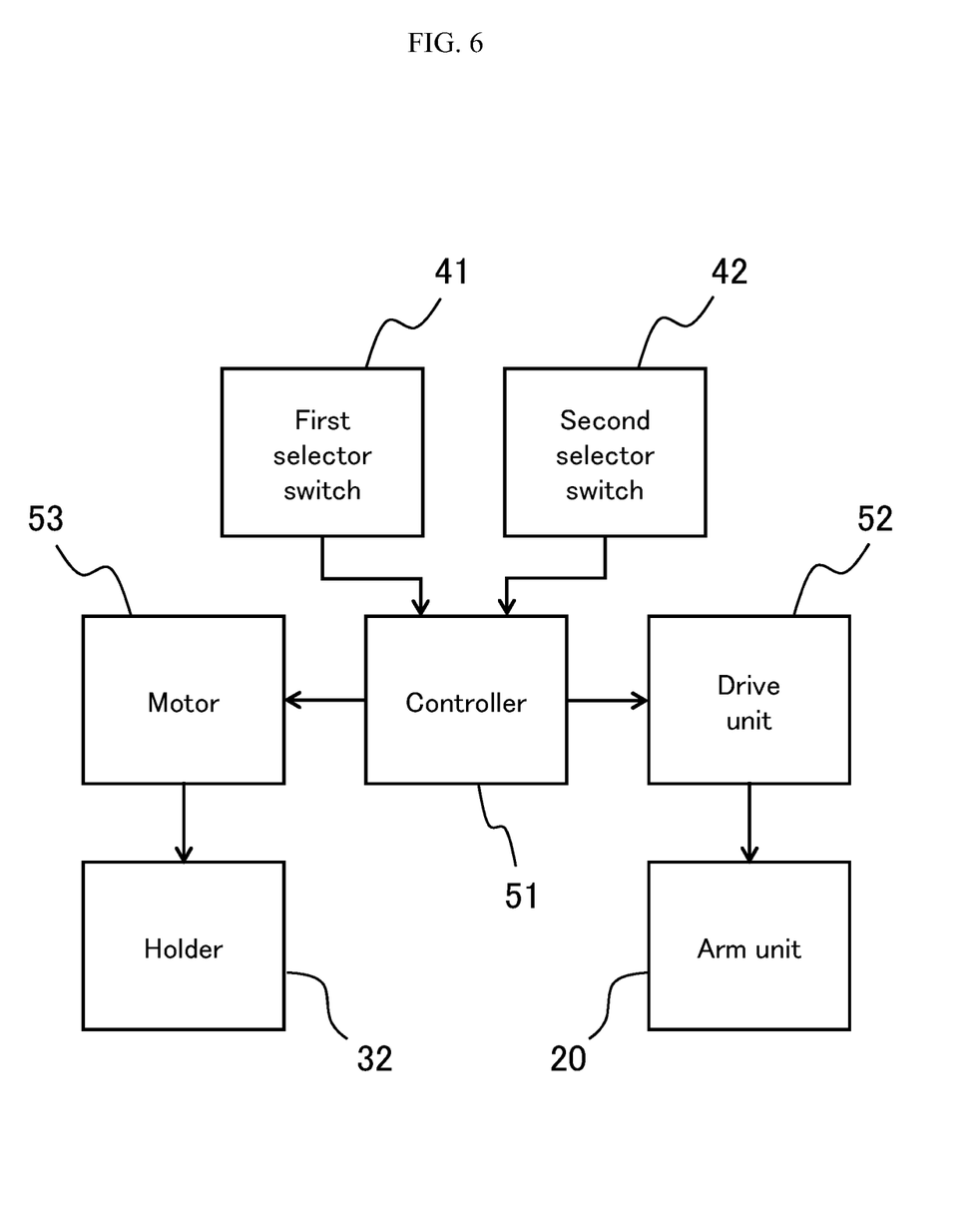
FIG. 6 is a functional block diagram of the medical robot according to some embodiments.

When one of the first selector switch 41 and the second selector switch 42 is pressed inside the main body portion 31, an operation signal is output to the controller 51 (see FIG. 6). When a predetermined time (e.g., 1 second) or more has elapsed from the start of pressing the selector switch, the controller 51 starts outputting to the drive unit 52 a control signal for switching from the control state to the manual state, and while this control signal is being output, the output of a drive signal from the drive unit 52 to the arm unit 20 is stopped, and the arm unit 20 is in a state in which it can be manually operated. That is, on the basis of the operation signal from one of the first selector switch 41 and the second selector switch 42, the controller 51 selectively switches between the control state in which the driving of the arm unit 20 is controlled and the manual state in which the control by the controller 51 is released.

Thus, the control state is switched to the manual state only when the selector switch 41, 42 is pressed for a predetermined time or longer, and the selector switch 41, 42 thereby serves as a prevention section that prevents the switching between the control state and the manual state due to contact with an interfering body located around the selector switch 41, 42.

Moreover, the state can be switched by pressing or releasing only one of the first selector switch 41 and the second selector switch 42; therefore, even when another arm unit or other member is located in the vicinity of any of the selector switches, the other selector switch can be visually recognized and operated, and the state can thus be changed reliably.

When the pressing of the pressed selector switch 41, 42 is released, the controller 51 outputs a control signal to the drive unit 52 to switch from the manual state to the control state and executes the control of returning from the manual state to the control state. The drive unit 52 switched to the control state drives each arm of the arm unit or units 20 in response to the control signal from the controller 51. The control by the controller 51 may include not only changing the posture and position of each arm, but also keeping the changed posture and position. On the other hand, in the manual state, the output of the control signal from the controller 51 to the drive unit 52 is stopped, and the practitioner can freely change the posture and position of each arm.

As illustrated in FIGS. 4A and 4B, each of the first selector switch 41 and the second selector switch 42 has an operation surface in a rectangular shape and is formed so as to protrude outward from the surface of the main body portion 31. Around these selector switches 41 and 42, rectangular frame portions 41a and 42a may be respectively provided so as to surround the selector switches 41 and 42 with a certain gap from each four sides. These frame portions 41a and 42a may also be formed so as to protrude outward from the surface of the main body portion 31, and the amount of protrusion thereof is approximately the same as the amount of protrusion of the first selector switch 41 and the second selector switch 42.

Therefore, while the practitioner can press the first selector switch 41 or the second selector switch 42 with his/her fingertip, even if an interfering body is liable to come into contact with any of the two selector switches 41 and 42, the prior contact with the frame portion 41a, 42a can prevent the selector switch 41, 42 from being pressed. Examples of such an interfering body include those other than the arm unit (first arm unit) which supports the holding body 30 provided with these switches, for example, one or more arm units (second arm units) arranged around the first arm unit or a member associated with the one or more arm units (second arm units), and an interfering body such as another member of the medical robot. Thus, erroneous switching between the control state and the manual state can be prevented. That is, the frame portion 41a, 42a serves as a prevention section that prevents the switching between the control state and the manual state due to contact with an interfering body located around the selector switch 41, 42.

The holding body 30 has the built-in motor 53 as a rotation mechanism that enables the holder 32 to rotate relative to the main body portion 31 of the holding body 30 (see FIG. 6). The motor 53 rotates the holder 32 about its central axis (axis along the second direction D2) in response to the control signal from the controller 51. This allows the held body, which is held by the holder 32, to rotate relative to the holding body 30 about the central axis along the extending direction of the held body (direction along the second direction D2). When the holder 32 is rotating, the holding body 30 keeps its posture and position, and the two selector switches 41 and 42 also keep their relative positions with respect to the holding body 30.

A modified example will be described below.

In some embodiments, when one of the first selector switch 41 and the second selector switch 42 is pressed for a predetermined time or longer, the control state may be switched to the manual state while when the pressing is released, the manual state is returned to the control state, but the switching of the state is not limited to this. For example, the control state and the manual state may be selectively switched each time one or both of the first selector switch 41 and the second selector switch 42 are pressed. This configuration enables quick switching between the states, and any of the states can be maintained even if the hand is released from the selector switch or switches.

In some embodiments, the switching between the control state and the manual state may be performed only when both the first selector switch 41 and the second selector switch 42 are operated at the same time. This configuration can prevent the state from changing due to erroneous contact with one of the two selector switches.

Another configuration including a regulating unit may also be possible. In this configuration, a sensor that detects that a surrounding arm unit or other interfering body approaches within a predetermined distance may be provided on the surface of the main body portion 31 as a prevention section that prevents switching between the control state and the manual state due to contact with an interfering body located around the holding body 30, and when the sensor detects the approach of an interfering body, the regulating unit regulates the operation of the selector switch.

Figure 10:
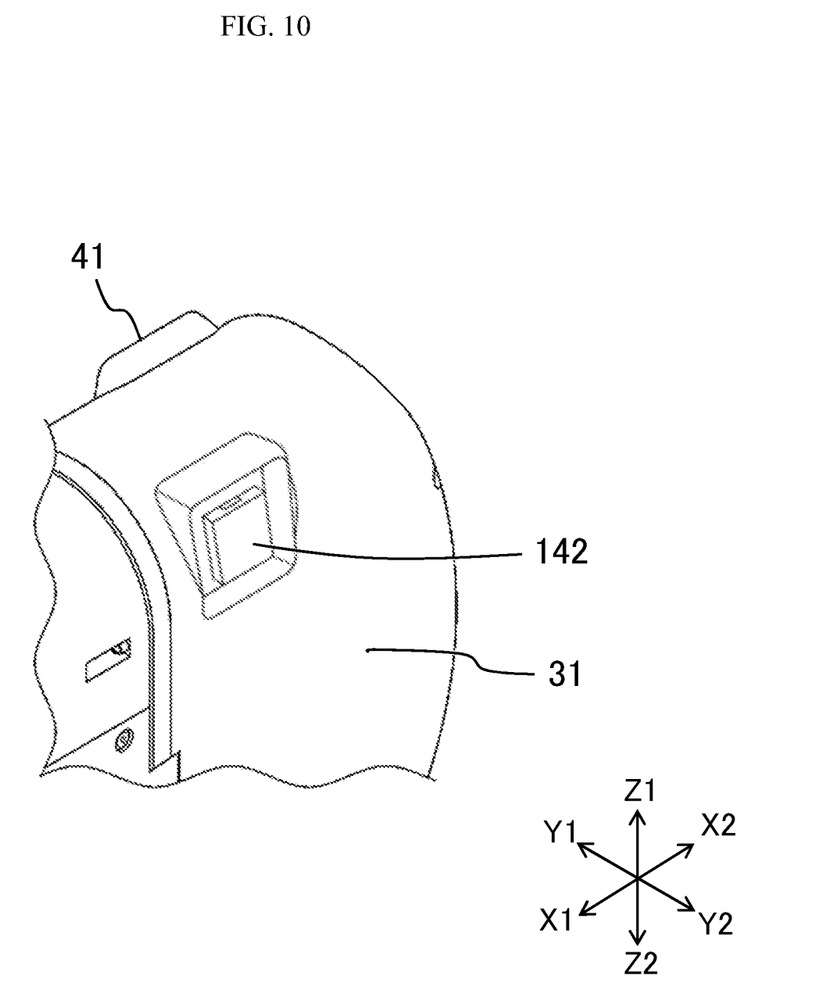
FIG. 10 is a perspective view illustrating another example of a selector switch, according to some embodiments.

Furthermore, the arrangement of the first selector switch 41 and the second selector switch 42 is not limited to the configuration illustrated in FIGS. 1 to 5. For example, as illustrated in FIG. 10, a second selector switch 142 may be displaced forward (X1 side) from the first selector switch 41 so that the positions of the two switches 41 and 142 are displaced from each other in the front-rear direction (X1-X2 direction). By arranging the switches asymmetrically in this way, it is possible to perform the treatment efficiently depending on the orientation of the holding body 30, the orientation of the treatment tool or other held body, the positional relationship with another arm unit or another peripheral device, the orientation of the practitioner's hand holding the holding body 30, the dominant hand of the practitioner, etc.

Various embodiments have been described above with reference to the drawings. However, it is to be understood that the present disclosure is not limited to the above embodiments, but various changes and modifications may be made therein without departing from the spirit and scope thereof as set forth in appended claims.

What is claimed is:

1. A medical robot comprising:
an arm unit;
a controller that controls driving of the arm unit;
a holding body that is connected to the arm unit at a connection portion of the holding body and that holds a held body; and
a selector switch provided on the holding body, the selector switch selectively switching between a control state in which the driving of the arm unit is controlled by the controller and a manual state in which control by the controller is released,
wherein the selector switch is disposed on one or both sides of a reference plane including an extending direction of the arm unit and an extending direction of the held body, and
the controller performs control to switch between the control state and the manual state based on an operation signal from the selector switch.

2. The medical robot according to claim 1, wherein the selector switch is provided on the holding body so as to be located on an opposite side to the held body with respect to the connection portion in the extending direction of the held body.

3. The medical robot according to claim 1, comprising a prevention section that prevents the switching between the control state and the manual state due to contact between the selector switch and an interfering body located around the selector switch.

4. The medical robot according to claim 3, wherein the prevention section is achieved by the selector switch, and the selector switch is configured to:
output a control signal for the controller to switch from the control state to the manual state when the selector switch is pressed inside the holding body; and
output a control signal for the controller to return from the manual state to the control state when pressing of the selector switch is released.

5. The medical robot according to claim 3, wherein the prevention section is achieved by the selector switch, and the selector switch is configured to output the operation signal for the controller to switch between the control state and the manual state each time the selector switch is pressed inside the holding body.

6. The medical robot according to claim 4, wherein the selector switch is a switch that operates when pressed for a predetermined time or longer.

7. The medical robot according to claim 4, wherein:
the selector switch comprises a first selector switch provided on one side of the reference plane and a second selector switch provided on another side of the reference plane, and
the controller switches between the control state and the manual state based on the operation signal from one of the first selector switch and the second selector switch.

8. The medical robot according to claim 7, wherein the controller is configured to:
provided that control of switching from the control state to the manual state is carried out based on the operation signal output from the first selector switch, carry out control of returning from the manual state to the control state when another version of the operation signal output from the first selector switch is input; and
provided that control of switching from the control state to the manual state is carried out based on the operation signal output from the second selector switch, carry out control of returning from the manual state to the control state when another version of the operation signal output from the second selector switch is input.

9. The medical robot according to claim 1, wherein the holding body includes a rotation mechanism that enables the held body to rotate relative to the holding body about an axis along the extending direction of the held body.

10. The medical robot according to claim 9, wherein the selector switch is provided so that a relative position with respect to the holding body is kept when the held body is rotating relative to the holding body.

11. The medical robot according to claim 3, wherein the arm unit is a first arm unit, and the medical robot further comprises at least one second arm unit in addition to the first arm unit,
wherein the interfering body includes the second arm unit located around the first arm unit.

12. The medical robot according to claim 11, wherein the second arm unit is provided with a holding body and a selector switch corresponding to the holding body and the selector switch for the first arm unit, respectively.

13. A medical robot comprising:
an arm;
a controller configured to drive the arm; and
a holding body provided at a distal end of the arm, the holding body comprising:
a holder provided at a front end in an extending direction of the holding body, and
a selector switch provided at a rear end in the extending direction of the holding body, wherein
the selector switch is configured to switch between a control state in which the driving of the arm is controlled by the controller and a manual state in which control by the controller is released.

14. The medical robot according to claim 13, wherein the selector switch is located on an upper part of the holding body opposite of the arm.

15. The medical robot according to claim 13, wherein the holding body further comprises:
a frame portion surrounding the selector switch and protruding outward from a surface of the holding body to prevent contact of an interfering body with the selector switch.

16. The medical robot according to claim 13, wherein the holding body further comprises a motor configured to rotate the holder body about an axis along the extending direction of the held body.

17. A medical robot comprising:
an arm;
a controller configured to drive the arm; and
a holding body provided at a tip of the arm, the holding body comprising:
a holder provided at a front end in an extending direction of the holding body, and a selector switch provided at a rear end in the extending direction of the holding body, wherein:
the selector switch is configured to switch between a control state in which the driving of the arm is controlled by the controller and a manual state in which control by the controller is released, and
the selector switch comprises a first selector switch for the control state provided on one side of the rear end of the holding body and a second selector switch for the manual state provided on another side of the rear end of the holding body.

18. The medical robot according to claim 17, wherein the second selector switch is aligned with the first selector switch in the extending direction of the holding body.

19. The medical robot according to claim 17, wherein the second selector switch is offset from the first selector switch in the extending direction of the holding body.

\* \* \* \* \*